United States Patent [19]
Kéri et al.

[11] Patent Number: 5,480,870
[45] Date of Patent: Jan. 2, 1996

[54] TUMOR GROWTH-INHIBITING SOMATOSTATIN ANALOGUES, PHARMACEUTICAL COMPOSITIONS CONTAINING THEM AND PROCESS FOR PREPARING SAME

[75] Inventors: György Kéri; Imre Mező; Anikó Horváth; Zsolt Vadász; István Teplán; Ágnes Balogh; Orsolya Csuka; Gyöngyi Bökönyi; Balás Szőke, all of Budapest; Judit Horváth, Pécs; Miklós Idei; János Seprődi, both of Budapest, all of Hungary

[73] Assignee: Biosignal Kutato-Fejlesztokft, Budapest, Hungary

[21] Appl. No.: 233,558

[22] Filed: Apr. 26, 1994

Related U.S. Application Data

[63] Continuation of Ser. No. 772,808, Oct. 8, 1991, abandoned.

[30] Foreign Application Priority Data

Jan. 25, 1991 [HU] Hungary ..................... 272/91

[51] Int. Cl.$^6$ .................... A61K 38/00; C07K 7/06; C07K 14/655
[52] U.S. Cl. .................. 514/16; 530/328; 530/329
[58] Field of Search ................... 530/328, 329; 514/16

[56] References Cited

FOREIGN PATENT DOCUMENTS 9109056  6/1991  WIPO.

OTHER PUBLICATIONS

Dermer, Biotechnology vol. 12, Mar. 1994.
Lamberts et al, *The New England Journal of Medicine*, vol. 313 No. 25, 1985, pp. 1576–1580.
Schally, *Proc' Natl. Acad. Sci*, vol. 84, pp. 7275–7279, 1987.
Han, et al, *Cancer Research*, vol. 47, 1566–1570. 1987.
Veber, et al, Nature, vol. 292, pp. 55–58, 2 Jul. 1981.
Taylor, et al, *Biochem and Biophysical Res. Comm*, v. 153, No. 1, 1988 pp. 81–86.
Brazeau, et al, Sci 179, 77 1973.
Murphy, et al, vol. 132, No. 3, pp. 922–928, 1985.
Cai, et al, Proc. Natl. Acad. Sci vol. 83, pp. 1896–1900. 1986.
Schally, Andrew V., "Oncological Applications of Somatostatin Analogues", Dec. 15, 1988, *Cancer Research*, vol. 48, pp. 6977–6985.
Evers et al., "Somatostatin and Analogues in the Treatment of Cancer", Mar. 1991, *Annals of Surgery*, vol. 213, No. 3.

*Primary Examiner*—Jill Warden
*Assistant Examiner*—Sg Marshall
*Attorney, Agent, or Firm*—Keil & Weinkauf

[57] ABSTRACT

The invention relates to tumor-inhibiting heptapeptide and octapeptide amide derivatives and to a method of treating mammals, including men, suffering from tumors or from the excessive secretion of insulin, glucagon or growth hormone using these compounds.

9 Claims, No Drawings

SEQUENCE LISTING ( 1 ) GENERAL INFORMATION:

( i i i ) NUMBER OF SEQUENCES: 27

( 2 ) INFORMATION FOR SEQ ID NO: 1:

( i ) SEQUENCE CHARACTERISTICS:
        ( A ) LENGTH: 8 amino acids
        ( B ) TYPE: amino acid
        ( D ) TOPOLOGY: unknown (i i) MOLECULE TYPE: peptide (x i) SEQUENCE DESCRIPTION: SEQ ID NO: 1:

Xaa Tyr Tyr Xaa Lys Val Phe Trp
1               5

(2) INFORMATION FOR SEQ ID NO:2:

(i) SEQUENCE CHARACTERISTICS:
        (A) LENGTH: 8 amino acids
        (B) TYPE: amino acid
        (D) TOPOLOGY: unknown (i i) MOLECULE TYPE: peptide (x i) SEQUENCE DESCRIPTION: SEQ ID NO: 2:

Xaa Cys Tyr Xaa Lys Val Cys Thr
1               5

(2) INFORMATION FOR SEQ ID NO:3:

(i) SEQUENCE CHARACTERISTICS:
        (A) LENGTH: 7 amino acids
        (B) TYPE: amino acid
        (D) TOPOLOGY: unknown (i i) MOLECULE TYPE: peptide (x i) SEQUENCE DESCRIPTION: SEQ ID NO: 3:

Xaa Cys Tyr Xaa Lys Cys Thr
1               5

(2) INFORMATION FOR SEQ ID NO:4:

(i) SEQUENCE CHARACTERISTICS:
        (A) LENGTH: 8 amino acids
        (B) TYPE: amino acid
        (D) TOPOLOGY: unknown (i i) MOLECULE TYPE: peptide (x i) SEQUENCE DESCRIPTION: SEQ ID NO: 4:

Xaa Cys Tyr Xaa Lys Leu Cys Thr
1               5

(2) INFORMATION FOR SEQ ID NO:5:

(i) SEQUENCE CHARACTERISTICS:
        (A) LENGTH: 8 amino acids
        (B) TYPE: amino acid
        (D) TOPOLOGY: unknown (i i) MOLECULE TYPE: peptide (x i) SEQUENCE DESCRIPTION: SEQ ID NO: 5:

Xaa Cys Tyr Xaa Lys Val Cys Thr
1               5

(2) INFORMATION FOR SEQ ID NO:6:

(i) SEQUENCE CHARACTERISTICS:
        (A) LENGTH: 8 amino acids
        (B) TYPE: amino acid
        (D) TOPOLOGY: unknown (i i) MOLECULE TYPE: peptide (x i) SEQUENCE DESCRIPTION: SEQ ID NO: 6:

```
Xaa Cys Tyr Xaa Lys Val Cys Thr
 1               5
```

( 2 ) INFORMATION FOR SEQ ID NO:7:

( i ) SEQUENCE CHARACTERISTICS:
    ( A ) LENGTH: 8 amino acids
    ( B ) TYPE: amino acid
    ( D ) TOPOLOGY: unknown ( i i ) MOLECULE TYPE: peptide ( x i ) SEQUENCE DESCRIPTION: SEQ ID NO: 7:

```
Xaa Cys Tyr Xaa Lys Val Cys Thr
 1               5
```

( 2 ) INFORMATION FOR SEQ ID NO:8:

( i ) SEQUENCE CHARACTERISTICS:
    ( A ) LENGTH: 8 amino acids
    ( B ) TYPE: amino acid
    ( D ) TOPOLOGY: unknown ( i i ) MOLECULE TYPE: peptide ( x i ) SEQUENCE DESCRIPTION: SEQ ID NO: 8:

```
Xaa Cys Tyr Xaa Lys Val Cys Thr
 1               5
```

( 2 ) INFORMATION FOR SEQ ID NO:9:

( i ) SEQUENCE CHARACTERISTICS:
    ( A ) LENGTH: 8 amino acids
    ( B ) TYPE: amino acid
    ( D ) TOPOLOGY: unknown ( i i ) MOLECULE TYPE: peptide ( x i ) SEQUENCE DESCRIPTION: SEQ ID NO: 9:

```
Xaa Cys Tyr Xaa Lys Val Cys Thr
 1               5
```

( 2 ) INFORMATION FOR SEQ ID NO:10:

( i ) SEQUENCE CHARACTERISTICS:
    ( A ) LENGTH: 8 amino acids
    ( B ) TYPE: amino acid
    ( D ) TOPOLOGY: unknown ( i i ) MOLECULE TYPE: peptide ( x i ) SEQUENCE DESCRIPTION: SEQ ID NO: 10:

```
Xaa Tyr Tyr Xaa Lys Val Phe Trp
 1               5
```

( 2 ) INFORMATION FOR SEQ ID NO:11:

( i ) SEQUENCE CHARACTERISTICS:
    ( A ) LENGTH: 9 amino acids
    ( B ) TYPE: amino acid
    ( D ) TOPOLOGY: unknown ( i i ) MOLECULE TYPE: peptide ( x i ) SEQUENCE DESCRIPTION: SEQ ID NO: 11:

```
Xaa Ala Tyr Tyr Xaa Lys Val Phe Trp
 1               5
```

( 2 ) INFORMATION FOR SEQ ID NO:12:

( i ) SEQUENCE CHARACTERISTICS:
        ( A ) LENGTH: 8 amino acids
        ( B ) TYPE: amino acid
        ( D ) TOPOLOGY: unknown ( i i ) MOLECULE TYPE: peptide ( x i ) SEQUENCE DESCRIPTION: SEQ ID NO: 12:

Xaa Cys His Xaa Lys Val Cys Thr
1               5

( 2 ) INFORMATION FOR SEQ ID NO:13:

( i ) SEQUENCE CHARACTERISTICS:
        ( A ) LENGTH: 8 amino acids
        ( B ) TYPE: amino acid
        ( D ) TOPOLOGY: unknown ( i i ) MOLECULE TYPE: peptide ( x i ) SEQUENCE DESCRIPTION: SEQ ID NO: 13:

Xaa Cys Tyr Xaa Xaa Val Cys Thr
1               5

( 2 ) INFORMATION FOR SEQ ID NO:14:

( i ) SEQUENCE CHARACTERISTICS:
        ( A ) LENGTH: 8 amino acids
        ( B ) TYPE: amino acid
        ( D ) TOPOLOGY: unknown ( i i ) MOLECULE TYPE: peptide ( x i ) SEQUENCE DESCRIPTION: SEQ ID NO: 14:

Xaa Cys Tyr Xaa Lys Leu Cys Thr
1               5

( 2 ) INFORMATION FOR SEQ ID NO:15:

( i ) SEQUENCE CHARACTERISTICS:
        ( A ) LENGTH: 8 amino acids
        ( B ) TYPE: amino acid
        ( D ) TOPOLOGY: unknown ( i i ) MOLECULE TYPE: peptide ( x i ) SEQUENCE DESCRIPTION: SEQ ID NO: 15:

Xaa Cys Tyr Xaa Lys Val Cys Thr
1               5

( 2 ) INFORMATION FOR SEQ ID NO:16:

( i ) SEQUENCE CHARACTERISTICS:
        ( A ) LENGTH: 8 amino acids
        ( B ) TYPE: amino acid
        ( D ) TOPOLOGY: unknown ( i i ) MOLECULE TYPE: peptide ( x i ) SEQUENCE DESCRIPTION: SEQ ID NO: 16:

Xaa Cys Tyr Xaa Lys Pro Cys Thr
1               5

( 2 ) INFORMATION FOR SEQ ID NO:17:

( i ) SEQUENCE CHARACTERISTICS:
        ( A ) LENGTH: 8 amino acids (B) TYPE: amino acid
                (D) TOPOLOGY: unknown (ii) MOLECULE TYPE: peptide (xi) SEQUENCE DESCRIPTION: SEQ ID NO: 17:

Xaa Cys Tyr Xaa Lys Xaa Cys Thr
1                   5

(2) INFORMATION FOR SEQ ID NO:18:

(i) SEQUENCE CHARACTERISTICS:
                (A) LENGTH: 8 amino acids
                (B) TYPE: amino acid
                (D) TOPOLOGY: unknown (ii) MOLECULE TYPE: peptide (xi) SEQUENCE DESCRIPTION: SEQ ID NO: 18:

Xaa Cys Tyr Xaa Lys Val Cys Trp
1                   5

(2) INFORMATION FOR SEQ ID NO:19:

(i) SEQUENCE CHARACTERISTICS:
                (A) LENGTH: 8 amino acids
                (B) TYPE: amino acid
                (D) TOPOLOGY: unknown (ii) MOLECULE TYPE: peptide (xi) SEQUENCE DESCRIPTION: SEQ ID NO: 19:

Xaa Cys Tyr Xaa Lys Val Cys Thr
1                   5

(2) INFORMATION FOR SEQ ID NO:20:

(i) SEQUENCE CHARACTERISTICS:
                (A) LENGTH: 8 amino acids
                (B) TYPE: amino acid
                (D) TOPOLOGY: unknown (ii) MOLECULE TYPE: peptide (xi) SEQUENCE DESCRIPTION: SEQ ID NO: 20:

Xaa Cys Phe Xaa Lys Thr Cys Trp
1                   5

(2) INFORMATION FOR SEQ ID NO:21:

(i) SEQUENCE CHARACTERISTICS:
                (A) LENGTH: 8 amino acids
                (B) TYPE: amino acid
                (D) TOPOLOGY: unknown (ii) MOLECULE TYPE: peptide (xi) SEQUENCE DESCRIPTION: SEQ ID NO: 21:

Xaa Cys Tyr Xaa Lys Val Cys Thr
1                   5

(2) INFORMATION FOR SEQ ID NO:22:

(i) SEQUENCE CHARACTERISTICS:
                (A) LENGTH: 8 amino acids
                (B) TYPE: amino acid
                (D) TOPOLOGY: unknown (ii) MOLECULE TYPE: peptide ( x i ) SEQUENCE DESCRIPTION: SEQ ID NO: 22:

Xaa Cys Tyr Xaa Lys Val Cys Trp
1               5

( 2 ) INFORMATION FOR SEQ ID NO:23:

( i ) SEQUENCE CHARACTERISTICS:
        ( A ) LENGTH: 8 amino acids
        ( B ) TYPE: amino acid
        ( D ) TOPOLOGY: unknown ( i i ) MOLECULE TYPE: peptide ( x i ) SEQUENCE DESCRIPTION: SEQ ID NO: 23:

Xaa Cys Tyr Xaa Lys Val Cys Thr
1               5

( 2 ) INFORMATION FOR SEQ ID NO:24:

( i ) SEQUENCE CHARACTERISTICS:
        ( A ) LENGTH: 8 amino acids
        ( B ) TYPE: amino acid
        ( D ) TOPOLOGY: unknown ( i i ) MOLECULE TYPE: peptide ( x i ) SEQUENCE DESCRIPTION: SEQ ID NO: 24:

Xaa Xaa Tyr Xaa Lys Val Xaa Trp
1               5

( 2 ) INFORMATION FOR SEQ ID NO:25:

( i ) SEQUENCE CHARACTERISTICS:
        ( A ) LENGTH: 8 amino acids
        ( B ) TYPE: amino acid
        ( D ) TOPOLOGY: unknown ( i i ) MOLECULE TYPE: peptide ( x i ) SEQUENCE DESCRIPTION: SEQ ID NO: 25:

Xaa Tyr Tyr Xaa Lys Val Phe Trp
1               5

( 2 ) INFORMATION FOR SEQ ID NO:26:

( i ) SEQUENCE CHARACTERISTICS:
        ( A ) LENGTH: 8 amino acids
        ( B ) TYPE: amino acid
        ( D ) TOPOLOGY: unknown ( i i ) MOLECULE TYPE: peptide ( x i ) SEQUENCE DESCRIPTION: SEQ ID NO: 26:

Xaa Ala Tyr Xaa Lys Val Phe Trp
1               5

( 2 ) INFORMATION FOR SEQ ID NO:27:

( i ) SEQUENCE CHARACTERISTICS:
        ( A ) LENGTH: 8 amino acids
        ( B ) TYPE: amino acid
        ( D ) TOPOLOGY: unknown ( i i ) MOLECULE TYPE: peptide ( x i ) SEQUENCE DESCRIPTION: SEQ ID NO: 27:

Xaa Ala Tyr Xaa Lys Val Phe Trp

TUMOR GROWTH-INHIBITING SOMATOSTATIN ANALOGUES, PHARMACEUTICAL COMPOSITIONS CONTAINING THEM AND PROCESS FOR PREPARING SAME

This application is a continuation of application Ser. No. 07/772,808, filed on Oct. 8, 1991, now abandoned.

The invention relates to novel octapeptide amide derivatives of the general formula (I),

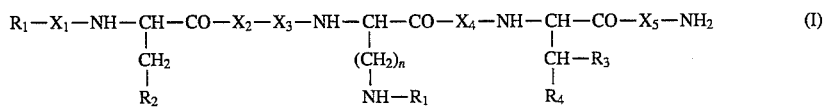 (I)

wherein $X_1$ stands for an aromatic D-amino acid residue or a derivative thereof ring-substituted by halogen or hydroxyl; or a D-phenylglycyl, p-hydroxyphenylglycyl, o-aminobenzoyl, m-aminobenzoyl, D-tetra-hydroisoquinolylcarbonyl, sarcosylalanyl group; or an

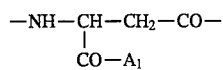

group, wherein $A_1$ means a primary or secondary aromatic or aliphatic amino group or an alkoxy, aryloxy or aralkyloxy group;

$X_2$ represents an aromatic D-amino acid residue or a derivative thereof ring-substituted by halogen or hydroxyl group; or a histidyl group;

$X_3$ means D-tryptophyl, o-aminobenzoyl, m-amino-benzoyl, aspartyl, D-aspartyl, β-aspartyl, β-D-aspartyl, aminosuccinyl group; or an

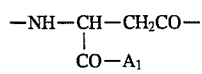

group, wherein $A_1$ is as defined above;

$X_4$ stands for an amino acid residue bearing an alkyl or aralkyl side chain, or a derivative thereof substituted by a hydroxyl or methyl group in β-position; or a prolyl or β-alanyl group; or a valence bond;

$X_5$ means an aromatic amino acid residue or a derivative thereof ring-substituted by halogen or hydroxyl group; or a threonyl group;

$R_1$ represents hydrogen or an $A_2$—CO— group, wherein $A_2$ means hydrogen or a $C_{1-4}$ alkyl group optionally substituted by halogen;

$R_2$ means hydrogen, —S—, —S-acetamidomethyl, phenyl or p-hydroxyphenyl group;

$R_3$ stands for hydrogen or hydroxyl group;

$R_4$ means a phenyl or p-hydroxyphenyl group; or —S— or —S-acetamidomethyl group when the meaning of $R_2$ is the same group; or a methyl group when $R_3$ is hydroxyl group, and n is 1, 2, 3 or 4, as well as their salts and pharmaceutical compositions containing these compounds.

According to an other aspect of the invention there is provided a process for the preparation of the new compounds of general formula (I), their salts and pharmaceutical compositions containing same.

The abbreviations used in the same formulae are in agreement with the nomenclature accepted in the peptide chemistry, which has been published e.g. in J. Bioi. Chem. 241, 527 (1966). According to this the abbreviations occurring in the description are as follows:

| X | | -X- |
|---|---|---|
| Phe | phenylalanine | (phenylalanyl) |
| Trp | tryptophan | (tryptophyl) |
| Tyr | tyrosine | (tirosyl) |
| Sar | sarcosine | (sarcosyl) |
| Ala | alanine | (alanyl) |
| His | histidine | (histidyl) |
| Val | valine | (valyl) |
| Thr | threonin | (threonyl) |
| Pro | proline | (prolil) |
| Leu | leucine | (leucyl) |
| Cys | cysteine | (cysteinyl) |
| Phg | phenylglycine | (phenylglycyl) |
| Pop | p-hydroxyphenylglycine | (p-hydroxyphenylglycyl) |
| Aa | o-aminobenzoic acid anthranilic acid | (o-aminobenzoyl) (anthranilyl) |
| Mab | m-aminobenzoic acid | (m-aminobenzoyl) |
| Tic | tetrahydroisoquinoline-carboxylic acid | (tetrahydroisoquinolyl-carbonyl) |
| Asu | aminosuccinimide | (aminosuccinyl) |
| Ac | acetyl | |
| Boc | tertiary butyloxycarbonyl | |
| Bop | benzotriazol-1-yl-oxy-tris(dimethylamino)-phosphonium hexafluorophosphate | |
| tBu | tertiary butyl | |
| Bzl | benzyl | |
| DCC | dicyclohexylcarbodiimide | |
| DCU | dicyclohexylurea | |
| DIC | diisopropylcarbodiimide | |
| DIPEA | diisopropylethylamine | |
| DMF | dimethylformamide | |
| Et | ethyl | |
| Fmoc | (9-fluorenylmethyl)oxycarbonyl | |
| For | formyl | |
| HPLC | high performance liquid chromatography | |
| Me | methyl | |
| ONP | p-nitrophenyl | |
| Opcp | pentachlorophenyl | |
| Opfp | pentafluorophenyl | |
| Ph | phenyl | |
| TEA | triethylamine | |
| TEAA | triethylammonium acetate | |
| TEAP | triethylammonium phosphate | |
| TFA | trifluoroacetic acid | |
| Tfa | trifluoroacetyl | |
| THF | tetrahydrofuran | |
| TLC | thin layer chromatography | |
| Tos | tosyl | |
| UV | ultraviolet | |
| Z | benzyloxycarbonyl. | |

Somatostatin, a cyclic tetradecapeptide (SRIF), being an inhibitor of secretion of the growth hormone (GH) was originally isolated from the hypothalamus [Brazeau et al.: Science 179, 77 (1973)]. Somatostatin has a very broad spectrum of biological effects, participates in a high number of biological processes and in the majority of cases it plays a role of an inhibitory factor (it inhibits e.g. the release of prolactin, insulin, glucagon, gastrin, secretin and cholecystoquinine) [S. Reichlin: Somatostatin, N. Eng. J. Med. 309, 1495 and 1556 (1983)].

One of the most important effects of somatostatin being a growth-inhibiting factor consists in its capability to influence various forms of pathological cell growth. It is well known from the literature that it exerts an inhibitory action on the growth of cancerous cells [A. V. Schally: Cancer Rs. 48, 6977 (1988); Taylor et al.: Biochem. Biophys. Res. Commun. 153, 81 (1988)]. Likely, somatostatin exerts its antagonizing action on growth factors related to cancerous processes. It has been shown by recent investigations that somatostatin and some somatostatin analogues are capable to activate the tyrosine phosphatase enzyme which antagonizes the effect of tyrosine kinases playing a very important role in the tumorous transformation [A. V. Schally: Cancer Res. 48, 6977 (1988)]. The importance of tyrosine kinases is supported by the fact that the majority of oncogens codes for tyrosine kinase and the major part of the growth factor receptors is tyrosine kinase [Yarden et al.: Ann. Rev. Biochem. 57, 443 (1989)].

Native somatostatin has a very short duration of effect in vivo since it is rapidly inactivated by endo- and exopeptidases. A high number of novel analogues have been prepared in order to enhance the duration of effect, biological activity and selectivity of this hormone. Most of the active analogues contain a cycle and a peptide chain which is shorter than the original one. The first cyclic hexapeptide showing the whole effects of somatostatin was synthetized by Veber et al. [Nature 292, 55 (1981)]. As a continuation newer and more effective cyclic hexa- and octapeptides have been synthetized which possess the whole spectrum of effects of somatostatin [Veber et al.: Life Sci. 34, 1371 (1984); Murphy et al.: Biochem. Biophys. Res. Commun. 132, 922 (1985); Cai et al.: Proc. Natl. Acad. Sci. USA 83, 1896 (1986)].

The aim of the present invention is to synthetize novel somatostatin analogues showing a more advantagous and/or more selective biological action in comparison to that of the known compounds.

The invention is based on the recognition that the effect of octapeptide analogues of somatostatin can be strengthened when the amino acid in 1-position is replaced by a substituent of strongly hydrophobic character and having a structure inhibiting the activity of exopeptidases. This substitution can preferably be combined with the replacement of the amino acid in 3-position by various aromatic amino acids; or with the replacement of the amino acid in 4-position by an aromatic D-amino acid, aromatic aminocarboxylic acid, aminosuccinimide or a β-aspartyl group substituted on its α-carboxyl group; or with the replacement of the amino acid in 6-position by an amino acid, bearing an alkyl or aralkyl side chain, or substituted derivatives thereof or proline or β-alanine; or with omission of the amino acid in 6-position; or with replacement of the amino acid in 8-position by an aromatic amino acid or a ring-substituted derivative thereof or by threonine.

A further basis of the invention is the recognition that, when an anthranilyl [see formula (III)],

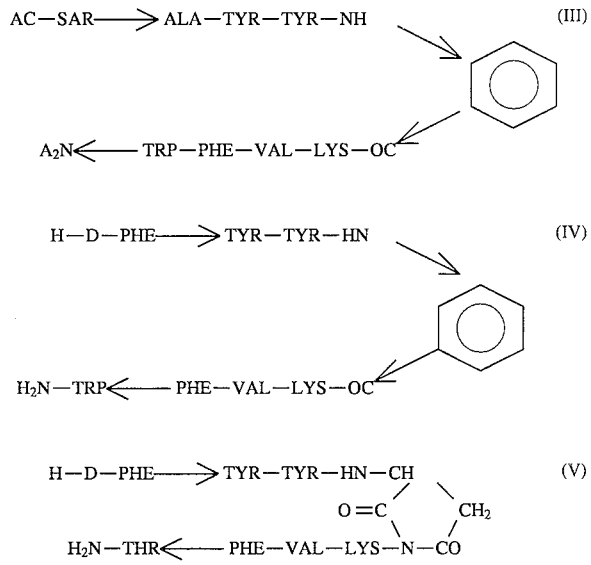

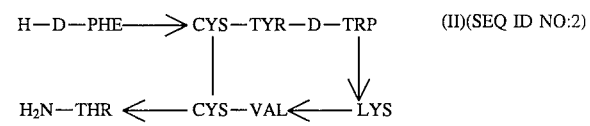

According to the invention, the novel octapeptide amides of general formula (I), wherein $X_1$, $X_2$, $X_3$, $X_4$, $X_5$, $R_1$, $R_2$, $R_3$, $R_4$ and n are as defined above, as well as their acid addition salts are prepared with the aid of the method of solid-phase peptide synthesis, by stepwise condensing the protected amino acids onto the solid resin carrier through carbodiimide or active ester coupling in the corresponding succession, then removing the final product from the solid carrier by acidic or alkaline cleavage, removing the protective groups from the amino acids simultaneously with or before or after cleavage from the resin and, if desired, converting an octapeptide amide of the general formula (I) thus obtained to an acid addition salt by reacting it with a pharmaceutically acceptable acid or, if desired, liberating the free base from an acid addition salt obtained by reacting it with an alkali.

It is suitable to use a benzhydrylamine resin or a chloromethylated polystyrene resin as solid carrier in the process of the invention. The final product containing protective groups can preferably be splitted off from the resin by using hydrogen fluoride and/or ammonolysis.

Preferred compounds of the invention include:

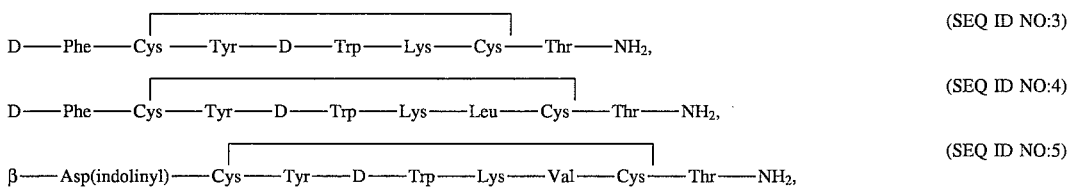

(SEQ ID NO:3)

(SEQ ID NO:4)

(SEQ ID NO:5)

D—Phe—Cys—Tyr—β—Asp(indolinyl)—Lys—Val—Cys—Thr—NH₂,  (SEQ ID NO:6)

D—Phg—Cys—Tyr—D—Trp—Lys—Val—Cys—Thr—NH₂,  (SEQ ID NO:7)

Tic—Cys—Tyr—D—Trp—Lys—Val—Cys—Thr—NH₂,  (SEQ ID NO:8)

β—Asp(NH—Ph)—Cys—Tyr—D—Trp—Lys—Val—Cys—Thr—NH₂,  (SEQ ID NO:9)

D—Phe—Tyr—Tyr—Aa—Lys—Val—Phe—Trp—NH₂,  (SEQ ID NO:10)

Ac—Sar—Ala—Tyr—Tyr—Aa—Lys—Val—Phe—Trp—NH₂,  (SEQ ID NO:11)

D—Phe—Cys—His—D—Trp—Lys—Val—Cys—Thr—NH₂,  (SEQ ID NO:12)

D—Phe—Cys—Tyr—D—Trp—Lys(Tfa)—Val—Cys—Thr—NH₂,  (SEQ ID NO:13)

D—Phe—Cys—Tyr—β—Asp(indolinyl)—Lys—Leu—Cys—Thr—NH₂,  (SEQ ID NO:14)

D—Phe—Cys—Tyr—Asu—Lys—Val—Cys—Thr—NH₂,  (SEQ ID NO:15)

D—Phe—Cys—Tyr—D—Trp—Lys—Pro—Cys—Thr—NH₂,  (SEQ ID NO:16)

D—Phe—Cys—Tyr—D—Trp—Lys—β—Ala—Cys—Thr—NH₂,  (SEQ ID NO:17)

Aa—Cys—Tyr—D—Trp—Lys—Val—Cys—Trp—NH₂,  (SEQ ID NO:18)

Pop—Cys—Tyr—D—Trp—Lys—Val—Cys—Thr—NH₂,  (SEQ ID NO:19)

Mab—Cys—Phe—D—Trp—Lys—Thr—Cys—Trp—NH₂,  (SEQ ID NO:20)

D-2-naphthyl-alanyl-Cys—Tyr—D—Trp—Lys—Val—Cys—Thr—NH₂,  (SEQ ID NO:21)

D—Phe—Cys—Tyr—Aa—Lys—Val—Cys—Trp—NH₂,  (SEQ ID NO:22)

D-2-naphthyl-alanyl-Cys—Tyr—Aa—Lys—Val—Cys—Thr—NH₂,  (SEQ ID NO:23)

Aa—Cys(Acm)—Tyr—D—Trp—Lys—Val—Cys(Acm)—Trp—NH₂,  (SEQ ID NO:24)

Pop—Tyr—Tyr—Aa—Lys—Val—Phe—Trp—NH₂,  (SEQ ID NO:25)

Ac—Sar—Ala—Tyr—Aa—Lys—Val—Phe—Trp—NH₂ and  (SEQ ID NO:26)

D—Phe—Ala—Tyr—Aa—Lys—Val—Phe—Trp—NH₂.  (SEQ ID NO:27)

The compounds of general formula (I) exert valuable pharmaceutical properties. They inhibit tumour growth as well as the proliferation and/or keratinisation of epidermal cells (e.g. psoriasis) and the secretion of insulin, glucagon and growth hormone.

The invention further relates to pharmaceutical compositions containing a compound of the general formula (I) or a pharmaceutically acceptable acid addition salt thereof as active ingredient together with carriers and/or additives commonly used in the pharmaceutical practice.

The pharmaceutical compositions of the present invention can be prepared by methods known per se by admixing the active ingredient with suitable inert solid or liquid carriers and bringing the mixture to the desired form.

The pharmaceutical compositions of the present invention may be suitable for oral administration e.g. as tablets, pills, coated pills, dragées, solid or soft gelatin capsules, solutions, emulsions or suspensions, parenteral administration e.g. as injection solutions, rectal administration e.g. as suppositories or may be in the form of a cream, gel or spray for application to the skin.

For the preparation of tablets, coated tablets, dragées and solid gelatine capsules e.g. lactose, corn starch, potatoe starch, talc, magnesium carbonate, magnesium stearate, calcium carbonate, stearic acid, the salts thereof, etc. can be used as carriers. For the soft gelatine capsules e.g. vegetable oils, fats, waxes or polyols of suitable consistency can be used as carriers. For the preparation of solutions and syrups e.g. water, polyols (polyethylene glycol), saccharose or glucose can be used as carriers. The injection solutions can comprise e.g. water, alcohols, polyols, glycerol or vegetable oils as carriers. The suppositories can be prepared with the aid of e.g. oils, waxes, fats or polyols of suitable consistency.

In addition, the pharmaceutical formulations may comprise auxiliary agents usually applied in pharmaceutical industry, e.g. wetting and sweeting agents, aroma substances, salts causing the change of osmotic pressure, buffers, etc.

The invention also relates to a method for treating a tumour disease and inhibiting the tyrosine kinase activity, the proliferation and/or keratinisation of epidermal cells (e.g. psoriasis) and the secretion of insulin, glucagon and growth hormone. This method comprises administering a therapeutically effective amount of an active ingredient of the general formula (I) or a pharmaceutically acceptable acid addition salt thereof to the patient.

The somatostatin derivatives of general formula (I) were found to be active in the daily dosage range of 0.01 to 500 μg/kg of body-weight (hereinafter: μg/kg) on mice or 0.5 to 2000 μg/kg, preferably 50 to 300 μg/kg, on man, respectively. The daily dose of the compounds can vary within wide ranges depending on several factors, e.g. on the activity of the active ingredient, the patient's condition and age, the severity of the disease, etc. It has to be stressed that these dose values are only of informative character and the administered dose must always be determined by the physician therapeutist.

The main advantages of the invention are as follows:

a) The novel somatostatin derivatives of the invention can preferably be utilized to inhibit tumour growth or the activity of tyrosine kinase enzymes playing an important role in the tumorous transformation.

b) By using the new amino acid combinations of the invention analogues can be prepared which are useful also for regulating the release of growth hormone (GH), insulin, glucagon and prolactin and/or for inhibiting tumour growth.

c) From the analogues bearing an aminosuccinyl, o- and m-aminobenzoyl substitution, those containing no disulfide bridge do not exert any inhibitory effect on the GH release but inhibit the growth of tumour cells.

d) The new somatostatin derivatives according to the invention can be used to inhibit pathological processes, such as psoriasis, elicited by the pathological proliferation of skin cells.

e) The o- and m-aminobenzoyl substituents are devoid of any centre of asymmetry, therefore no racemization can occur during their synthesis. Thus, the preparation of the final product becomes easier and cheaper.

f) The preparation costs of o- and m-aminobenzoic acid are much lower than those of the D-amino acids playing a similar role in somatostatin analogues known up to now.

The invention is illustrated in detail by the following non-limiting Examples.

In the Examples, the compounds are prepared by methods commonly used in the solid-phase peptide synthesis (Stewart et al.: Solid Phase Peptide Synthesis, 2nd Edition, Pierce Chemical Company, Rockford, Ill., 1984). The individual amino acids are stepwise bound in the form of their Boc or Fmoc derivatives to a benzhydrylamine or chloromethylated polystyrene resin by the symmetric anhydride or active ester coupling or by the aid of DCC, DIC or BOP reagents.

The progress of the reaction is evaluated by the ninhydrin test [E. Kaiser et al.: Anal. Biochem. 34, 595 (1970)]. The acylation is repeated when a free amino group is detected. The time demand of coupling depends on the amino acids and varies between 1 and 16 hours.

Both the removal of protective groups and cleavage of the peptide from the resin are preferably carried out in a single step by using anhydrous liquid hydrogen fluoride [S. Sakakibara et al.: Bull. Chem. Soc. Japan 40, 2164 (1967)].

If desired, the crude product obtained by HF cleavage is cyclized.

The crude product is purified by using Sephadex chromatography and/or preparative HPLC method. The purity of the final product is examined by TLC, analytical HPLC and amino acid analysis. The TLC Rf values are determined on Kieselgel sheets (DC Alufolien, Merck) by using the solvent mixtures listed hereinafter:

1. Ethyl acetate/pyridine/acetic acid/water 30:20:6:11
2. Ethyl acetate/pyridine/acetic acid/water 60:20:6:11
3. Butanol/pyridine/acetic acid/water 60:20:6:11
4. n-Butanol/acetic acid/water 4:1:2
5. n-Butanol/acetic acid/water/ethyl acetate 1:1:1:1
6. n-Butanol/acetic acid/water 4:1:1
7. Isopropanol/1 molar acetic acid 2:1
8. Ethyl acetate/pyridine/acetic acid/water 5:5:1:3

Example 1

Preparation of

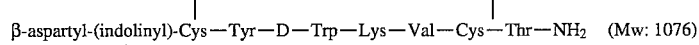

β-aspartyl-(indolinyl)-Cys—Tyr—D—Trp—Lys—Val—Cys—Thr—NH₂ (Mw: 1076) (SEQ ID NO:5)

0.47 g (0.25 mmol) of benzhydrylamine hydrochloride resin (0.54 milliequivalent/g) is swollen in methylene chloride ($CH_2Cl_2$) for 90 minutes, then the following cycle is repeated after each acylation carried out with the amino acids.

| Step | Reagents, procedure | Time of stirring (min) |
|---|---|---|
| 1 | $CH_2Cl_2$; 3 washings | 1 |
| 2 | Mixture containing 33% of TFA, 5% of anisole and 62% of $CH_2Cl_2$; cleavage | 1 |
| 3 | Mixture containing 33% of TFA, 5% of anisole and 62% of $CH_2Cl_2$; cleavage | 1 |
| 4 | $CH_2Cl_2$; 3 washings | 1 |
| 5 | Ethanol; 2 washings | 1 |
| 6 | $CH_2Cl_2$; 3 washings | 1 |
| 7 | Mixture containing 10% of TEA and 90% of $CH_2Cl_2$; 2 washings | 2 |
| 8 | $CH_2Cl_2$; 3 washings | 2 |
| 9 | Ethanol; 2 washings | 1 |
| 10 | $CH_2Cl_2$; 3 washings | 1 |
| 11 | 3 equivalents of Boc-amino acid dissolved in the mixture of $CH_2Cl_2$ and DMF as well as 3 equivalents of DCC or DIC dissolved in $CH_2Cl_2$; coupling | 60 minutes to 16 hours |
| 12 | $CH_2Cl_2$; 3 washings | 1 |
| 13 | Ethanol; 2 washings | 1 |

A ninhydrin test is made after each step. When the result is positive, the cycle is repeated from the 6th step.

0.25 mmol of β-Asp(indolinyl)-Cys(4-Me-Bzl)-Tyr(2-Br-Z)-D-Trp-Lys(Z)-Val-Cys(4-Me-Bzl)-Thr(Bzl) peptide resin is suspended in 3 ml of anisole containing 10% of p-cresol, and 30 ml of HF gas are condensed onto the mixture. After stirring at 0° C. for 45 minutes HF is removed, the residue is suspended in 200 ml of ethyl acetate, stirred for 15 minutes, then poured into 250 ml of ethyl acetate. After filtration the precipitate is filtered, washed with ethyl acetate, then the peptide is dissolved from the precipitate by filtration, using 500 ml of 95% gas-free acetic acid. Then 9.0 ml of 0.03 M iodine/methanol solution are dropped to the acetic acid solution until it becomes orange yellow. Thereafter, the solution is stirred for one hour. Zinc powder is cautiously added to the solution until the yellow colour disappears, then the zinc powder is filtered and the solution is evaporated. The solid residue is dissolved in 6 ml of 50% acetic acid and purified on a Sephadex G-25 column. The elution is followed by using UV absorption measured at 280 nm and TLC. The fractions containing the aimed product are collected, evaporated, then further purified by gradient elution in a preparative HPLC system (column: Whatman Partisil 10 ODS-3 22×250 mm; eluent A: 0.25 N TEAP, pH 2.24; eluent B: 80% of methanol with 20% of A). The pure product is desalinized by gradient elution, using 0.02 M NH$_4$OAc, pH 5 (eluent A) as well as 70% of methanol with 30% of eluent A (eluent B) to obtain 120 mg (43%) of final product. The physical characteristics of this compound are summarized in Table I, the biological effects are shown in Tables II, III, IV and V.

Example 2

Preparation of D-Phe-Cys-Tyr-D-Trp-Lys-Val-Cys-Thr-NH$_2$ (Mw: 1034) (SEQ ID NO: 7)

The aimed peptide is synthetized as described in Example 1, starting from 0.5 g (0.27 mmol) of benzhydrylamine hydrochloride resin (0.54 milliequivalent/g), splitted off from the resin, cyclized and purified by using Sephadex chromatography. Solvents used in the HPLC purification are: A: 0.1% TEAA, pH 4.2; B: 80% of methanol with 20% of A. The product is desalinized by several lyophilizations. In this way the aimed peptide is obtained in a yield of 54 mg (19.4%). The physical characteristics of this compound are summarized in Table I, the biological effects are shown in Tables II, III and IV.

Example 3

Preparation of (SEQ ID NO:3)

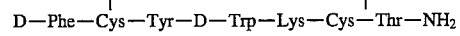

D—Phe—Cys—Tyr—D—Trp—Lys—Cys—Thr—NH$_2$ (Mw: 947)

Starting from 0.47 g (0.25 mmol) of benzhydrylamine hydrochloride resin (0.54 milliequivalent/g) the peptide is synthetized, cyclized and purified as described in Example 1 to give the final product in a yield of 80.5 mg (34%). The physical characteristics are summarized in Table I, the biological effects are shown in Tables II and III.

Example 4

Preparation of (SEQ ID NO:4)

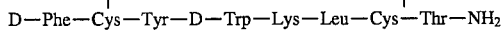

D—Phe—Cys—Tyr—D—Trp—Lys—Leu—Cys—Thr—NH$_2$ (Mw: 1060)

Starting from 0.47 g (0.25 mmol) of benzhydrylamine hydrochloride resin (0.54 milliequivalent/g) the aimed peptide is synthetized, cyclized and purified as described in Example 1 to obtain 106 mg (40%) of final product. The physical characteristics of this compound are summarized in Table I, the results of biological assays are shown in Tables II, III, IV and V.

Example 5

Preparation of

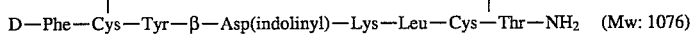

D—Phe—Cys—Tyr—β—Asp(indolinyl)—Lys—Leu—Cys—Thr—NH$_2$ (Mw: 1076) (SEQ ID NO:14)

Starting from 0.47 g (0.25 mmol) of benzhydrylamine hydrochloride resin the aimed peptide is synthetized, cyclized and purified as described in Example 1 to give 94 mg (35.5%) of final product. The physical characteristics of this compound are summarized in Table I, the results of biological assays are shown in Tables II, III, IV and V.

Example 6

Preparation of D-Phe-Tyr-Tyr-Aa-Lys-Val-Phe-Trp-NH$_2$ (Mw: 1192) (SEQ ID NO: 10)

Starting from 0.47 g (0.25 mmol) of benzhydrylamine hydrochloride resin the peptide is synthetized as described in Example 1. The D-Phe-Tyr(2-Br-Z)-Tyr(2-Br-Z)-Aa-Lys(2-Cl-Z)-Val-Phe-Trp peptide resin obtained after the last step is suspended in 3 ml of anisole, 30 ml of gaseous HF are condensed onto the mixture which is then stirred at 0° C. for 5 minutes. After removing the gaseous HF the residue is suspended in 200 ml of abs. ether, stirred for 15 minutes and after filtration the precipitate is washed with ether. Thereafter, the peptide is dissolved from the precipitate with 50% acetic acid, the solution is evaporated and the thus-obtained D-phe-Tyr-Tyr-Aa-Lys-Val-phe-Trp-NH$_2$ (SEQ ID NO: 10) octapeptide amide is purified by preparative HPLC. Eluent A: 0.25 N TEAP, pH 2.25; eluent B: mixture of 70% of acetonitrile and 30% of eluent A. The separation is carried out on the column mentioned in Example 1 by using a mixture containing 30% of eluent B and 70% of eluent A. The pure product is desalinized as described in Example 1 to obtain 89 mg (30%) of final product. The physical characteristics of this compound are summarized in Table I, the biological effects are shown in Tables II and III.

Example 7

Preparation of Ac-Sar-Ala-Tyr-Tyr-Aa-Lys-Val-Phe-Trp-NH$_2$ (Mw: 1217) (SEQ ID NO: 11)

The aimed peptide is prepared by using the process of Example 6 but an Ac-Sar group is coupled to the peptide resin in the last cycle. The cleavage of the product from the resin and the purification are also carried out as described in Example 6 to obtain 85 mg (28%) of final product. The physical characteristics of the compound are summarized in Table I whereas its biological effects are shown in Tables II, III and IV.

Example 8

Preparation of Pop-Tyr-Tyr-Aa-Lys-Val-Phe-Trp-NH$_2$ (Mw: 1194) (SEQ ID NO: 25)

This peptide is synthetized as described in Example 1, except that in the 11th step Bop reagent is used in an amount equal to the amino acid as activating agent for coupling the amino acid in the presence of an excess of DIPEA. After cleavage by HF and purification by chromatography, the final product is obtained as described in Example 6 with a yield of 105 mg (35%). The physical characteristics of the compound are summarized in Table I.

Example 9

Preparation of Aa-Cys(Acm)-Tyr-D-Trp-Lys-Val-Cys(Acm)-Trp-NH$_2$ (Mw: 1283) (SEQ ID NO: 24)

After swelling 0.47 g (0.25 mmol) of benzhydrylamine hydrochloride resin in methylene chloride for 90 minutes, the following cycle is repeated after each acylation carried out with the Fmoc-derivatives of the suitably protected amino acids:

| Step | Reagents, procedure | Time of stirring (minute) |
|---|---|---|
| 1 | DMF; 3 washings | 2 |
| 2 | Mixture containing 20% of piperidine and 80% of DMF; cleavage | 2 |
| 3 | Mixture containing 20% of piperidine and 80% of DMF; cleavage | 10 |
| 4 | DMF; 5 washings | 2 |
| 5 | Symmetric anhydride+ prepared from 3 equivalents of Fmoc-amino acid or Opfp ester; coupling | 60 |
| 6 | DMF; 3 washings | 2 |

+ = Preparation of the symmetric anhydride: 3 equivalents of Fmoc-amino acid are dissolved in a mixture of CH$_2$Cl$_2$ and DMF. After adding 1.5 equivalents of DCC the mixture is stirred at room temperature for 15 minutes. The DCU precipitate is filtered off, the solution is evaporated and the residue dissolved in DMF is used for coupling.

A ninhydrin test is made after each step. When a positive result is obtained, the cycle is repeated from the 5th step.

The Aa-Cys(Acm)-Tyr(tBu)-D-Trp-Lys(Boc)-Val-Cys(Acm)-Trp peptide resin obtained after the last step is treated with HF, purified and desalinized as described in Example 6 to obtain 147 mg (46%) of final product. The physical characteristics of the compound are summarized in Table I.

Examples 10 to 15

The compounds of the following formula, listed hereinafter, are prepared by using the process described in Examples 1 to 5.

A—Cys—B—D—Trp—C—E—Cys—Thr—NH$_2$

| Example | A | B | C | E | Code No. |
|---|---|---|---|---|---|
| 10 | β-Asp(NH-Ph) | Tyr | Lys | Val | TT 2-22 |
| 11 | Tic | Tyr | Lys | Val | MI 1811 |
| 12 | D-Phe | His | Lys | Val | MK 1-42 |
| 13 | D-Phe | Tyr | Lys (Tfa) | Val | TH 363 |
| 14 | D-Phe | Tyr | Lys | β-Ala | TT 2-18 |
| 15 | D-Phe | Tyr | Lys | Pro | TT 2-28 |

The physical characteristics of the above compounds are summarized in Table I, the results of biological assays are shown in Tables II, III and IV.

Examples 16 and 17

Compounds of the following formula are prepared as described in Example 6:

A—B—Tyr—Aa—Lys—Val—Phe—Trp—NH$_2$ (SEQ ID NO: 27)

| Example | A | B | Code No. |
|---|---|---|---|
| 16 | Ac—Sar | Tyr | AH32/2 |
| 17 | D—Phe | Ala | AH52 |

The physical characteristics of the above compounds are summarized in Table I, the results of biological assays are shown in Table II.

Examples 18 and 19

The following compounds are prepared by using the process described in Example 1:

(SEQ ID NO:22 or 23)

A—Cys—Tyr—Aa—Lys—Val—Cys—Trp—NH$_2$

In Example 18 "A" stands for a D-Phe group, in Example 19 for a D-2-naphthyl-alanyl group. The physical data of the compounds are summarized in Table I/A.

Example 20

The following compound is prepared by using the process described in Example 1:

(SEQ ID NO:18)

Aa—Cys—Tyr—D—Trp—Lys—Val—Cys—Trp—NH$_2$

The physical data of the compounds are summarized in Table I/A.

Example 21

(SEQ ID NO:15)

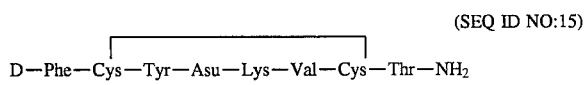

D—Phe—Cys—Tyr—Asu—Lys—Val—Cys—Thr—NH₂

The compound is prepared by using the process described in Example 1 with the exception that after coupling the Lys residue the neutralization is carried out with 5% diisopropylethylamine in dichloromethane, instead of using TEA. The side-chain protecting group (fluorenylmethyl ester) of Asp is removed from the protected peptide resin by stirring it for 2×20 minutes in a 1:1 mixture of DMF and piperidine. The formation of Asp-β-pentafluorophenyl ester is carried out by stirring the suspension of the peptide resin for 30 minutes in DMF with an excess of pentafluorophenol and diisopropyl carbodiimide. The peptide resin is filtered and washed with DMF. The aspartimide derivative is formed from the pentafluorophenyl ester derivative by stirring the peptide resin in DMF. The formation of the aspartimide ring is followed by measuring the released pentafluorophenol. The UV absorption of a small amount of the filtered reaction mixture is measured at 278 nm using DMF as control. The cleavage of the remaining protecting groups, the cleavage of the peptide from the resin, the formation of the disulfide bridge and the purification of the crude product are carried out using the process described in Example 1. The physical data of the compound are summarized in Table I/A.

The physical data of the compound are summarized in Table I/A.

The biological effects of the compounds according to the invention are supported by the tests described hereinafter.

Assay of the growth hormone (GH)

The release or inhibition, respectively, of the release of GH were measured on rat hypophysis by using the superfusion method [Vigh et al.: Peptides 5, 241 (1984)]. As control, the GH amount was considered which was released by the GH releasing hormone (GHRH) given in the same dose as the sample. The activity of the somatostatin analogue was expressed as the percentage of decrease or increase, respectively, in the GH amount released by GHRH (Table II).

Assay of the inhibition of cell division

The incorporation of [³H]-thymidine to tumour cells of various origin and measurement of the cell count were carried out according to the method of Kéri et al. [Tumor Biology 9, 315 (1988)]. The biological activity of the analogues was expressed as the percentage of inhibition of the labelled thymidine incorporation or increase in the count of untreated cells used as control (Table III).

Measurement of the tyrosine kinase activity

The tyrosine kinase activity was also determined according to the method of Kéri et al. [Tumor Biology 9, 315 (1988)]. The activity of the analogues was characterized on the basis of their inhibitory effect in comparison to the incorporation of ³²p isotope to untreated cells used as control (Table IV).

Study of effectivity of the compounds on the tumour growth in the metastasis model The anti-metastatic effect of the compounds was studied on Lewis lung tumour (LLT) cells in muscle-lung and spleen-liver metastasis model as well as on their immunoresistant cell variant (LLT-HH). These experiments were carried out on inbred $C_{57}B1$ mice of both sexes. The LLT was transplanted into the muscle for developing the muscle-lung metastasis model, whereas a suspension of the tumour cells was injected to the spleen to form the spleen-liver metastasis. The compounds to be tested were administered intraperitoneally (i.p.), intravenously (i.v.), orally (p.o.) or subcutaneously (s.c.) in 0.1 to 10 mg/kg doses daily 1 to 3 times in the 5th to 13th days. The therapeutic effect was evaluated on the basis of the number of metastases in such a way that a sample was taken in the spleen-liver model between the 10th and 14th days, in the muscle-lung model between the 17th and 18th days and the macroscopic metastases in the liver and lungs, respectively, were counted under a stereomicroscope. The efficiency of the compounds was expressed in percentage of the count of metastases determined in the control animals (Table V).

TABLE I

Physical characteristics of the compounds of the invention

| Example | M.p. (°C.) | $[\alpha]_D^{20*}$ | $R_f^1$ | $R_f^2$ | $R_f^3$ | $R_f^4$ | $R_f^5$ | $R_f^6$ | $R_f^7$ | $R_f^8$ |
|---|---|---|---|---|---|---|---|---|---|---|
| 1 |  | −53 | 0.62 | 0.19 | 0.61 | 0.55 |  | 0.56 | 0.81 |  |
| 2 |  | −93 | 0.63 | 0.19 | 0.63 | 0.55 |  | 0.58 | 0.81 |  |
| 3 |  | −98.2 | 0.55 |  |  | 0.41 |  | 0.36 | 0.73 |  |
| 4 |  | −43 | 0.65 | 0.22 | 0.66 | 0.59 |  | 0.61 | 0.81 |  |
| 5 |  | −63 | 0.61 | 0.19 | 0.64 | 0.51 |  | 0.55 | 0.16 |  |
| 6 | 156–160 | −19.6 |  |  |  |  | 0.83 | 0.69 |  | 0.88 |
| 7 | 168–172 | −34 |  |  |  |  | 0.70 | 0.60 | 0.70 | 0.60 |
| 8 |  |  |  |  |  |  | 0.80 | 0.60 |  | 0.90 |
| 9 | 138–140 | −47 |  | 0.27 |  |  | 0.84 | 0.40 |  | 0.81 |
| 10 |  |  | 0.63 | 0.26 |  | 0.72 |  |  |  |  |
| 11 |  | −57.4 | 0.63 | 0.22 | 0.64 | 0.51 |  | 0.55 | 0.80 |  |
| 12 |  | −116.2 | 0.43 | 0.04 | 0.35 | 0.36 |  | 0.14 | 0.16 |  |
| 13 |  | −68.6 | 0.85 | 0.63 | 0.76 | 0.75 |  | 0.78 | 0.93 |  |
| 14 |  | −30.8 | 0.60 | 0.01 | 0.54 | 0.48 |  | 0.43 | 0.80 |  |
| 15 |  | −63.4 | 0.57 | 0.12 | 0.48 | 0.41 |  | 0.36 | 0.73 |  |
| 16 |  |  | 0.57 | 0.25 | 0.58 |  |  | 0.57 |  |  |
| 17 |  |  |  |  |  |  | 0.80 | 0.60 |  | 0.90 |

*: c = 0.5 (0.1% acetic acid)

TABLE I/A

Physical data of compounds 18–21

| No. of example | $[\alpha]_D^+$ | $R_f^1$ | $R_f^2$ | $R_f^3$ | $R_f^4$ | $R_f^5$ | $R_f^6$ |
|---|---|---|---|---|---|---|---|
| 18 | | | | | | 0.61 | 0.38 |
| 19 | | 0.09 | | | | 0.74 | 0.49 |
| 20 | | 0.88 | | | | | 0.79 |
| 21 | −31.2 | | 0.13 | 0.51 | 0.41 | | |

+: c = 0.5 (0.1% acetic acid)

TABLE II

Change of GH release elicited by GHRH under effect of the analogues of the invention

| Code No. | Example | Change of GH release |
|---|---|---|
| TT 2-48 | 1 | −100 |
| TT 2-20 | 2 | −93 |
| TT 2-32 | 3 | 0 |
| TT 2-50 | 4 | −100 |
| MK 1-43 | 5 | +290 |
| AH 31 | 6 | +26 |
| AH 25 | 7 | −20 |
| MI 1811 | 11 | −85 |
| MK 1-42 | 12 | −100 |
| TT 2-18 | 14 | −10 |
| TT 2-28 | 15 | 0 |
| AH 32/2 | 16 | +9 |

TABLE III

Assay of the inhibition of cell division on various tumour cells

| Code No. | Example | Cell line+ | Dose (µg) | Inhibition (%) |
|---|---|---|---|---|
| TT 2-48 | 1 | HT 29 | 1 | 36 |
| | | HT 29 | 10 | 44 |
| | | MCF 7 | 10 | 46 |
| TT 2-20 | 2 | HT 29 | 20 | 27 |
| | | MCF 7 | 20 | 45 |
| TT 2-32 | 3 | HT 29 | 20 | 75 |
| | | DU 145 | 10 | 68 |
| | | PC 3 | 10 | 45 |
| TT 2-50 | 4 | HT 29 | 1 | 57 |
| | | HT 29 | 10 | 50 |
| | | MCF 7 | 10 | 31 |
| | | DU 145 | 10 | 36 |
| MK 1-43 | 5 | SW 620 | 10 | 68 |
| AH 31 | 6 | MCF 7 | 40 | 48 |
| AH 25 | 7 | HT 29 | 10 | 28 |

TABLE III-continued

Assay of the inhibition of cell division on various tumour cells

| Code No. | Example | Cell line+ | Dose (µg) | Inhibition (%) |
|---|---|---|---|---|
| | | MCF 7 | 20 | 24 |
| MI 1811 | 11 | MCF 7 | 10 | 21 |
| MK 1-42 | 12 | MCF 7 | 10 | 38 |
| | | MCF 7 | 20 | 44 |
| TH 363 | 13 | MCF 7 | 10 | 13 |
| | | MCF 7 | 20 | 19 |
| TT 2-18 | 14 | MCF 7 | 20 | 45 |
| | | HT 29 | 20 | 13 |

+HT 29: tumour cell line of human colon origin
MCF 7: tumour cell line of human breast origin
DU 145: tumour cell line of human prostate
PC 3: tumour cell line of human prostate
SW 620: tumour cell line of human colon origin?

TABLE IV

Assay of the tyrosine kinase activity

| Code No. | Example | Cell line+ | Dose (µg) | Inhibition (%) |
|---|---|---|---|---|
| TT 2-48 | 1 | HT 29 | 10 | 44 |
| TT 2-20 | 2 | HT 29 | 1 | 35 |
| | | HT 29 | 10 | 22 |
| TT 2-32 | 3 | SW 620 | 1 | 84 |
| | | SW 620 | 10 | 70 |
| TT 2-50 | 4 | HT 29 | 10 | 50 |
| | | HT 29 | 30 | 90 |
| MK 1-43 | 5 | HT 29 | 10 | 30 |
| | | HT 29 | 30 | 45 |
| AH 25 | 7 | HT 29 | 10 | 17 |
| | | HT 29 | 30 | 23 |
| MK 1-42 | 12 | HT 29 | 10 | inactive |
| | | HT 29 | 30 | inactive |

+ = HT 29: tumour cell line of human colon origin
SW 620: tumour cell line of human colon origin

TABLE V

Effect on the tumour growth in the metastasis model

| Code No. | Example | Count of metastases (%) related to control (100%) |
|---|---|---|
| TT 2-48 | 1 | 43 |
| TT 2-50 | 4 | 35 |
| MK 1-43 | 5 | 25 |
| TH 363 | 13 | 51 |

What we claim is:

1. A heptapeptide or octapeptide amide derivative selected from the group consisting of β-aspartyl-(indolinyl)-
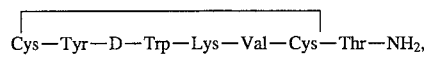
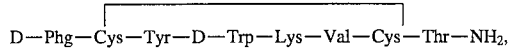
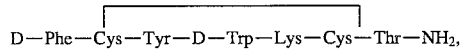
D—Phe—
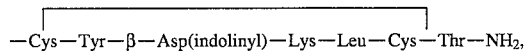
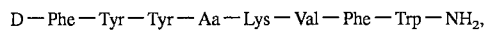
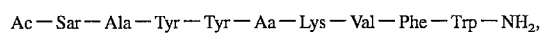
Aa—Cys(Acm)—Tyr—D—Trp—
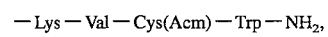
β—Asp(NH—Ph)—
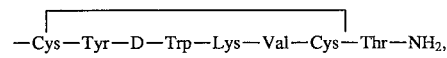
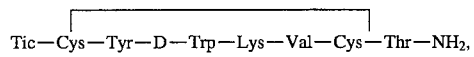
D—Phe—
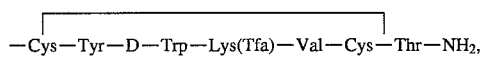
D—Phe—
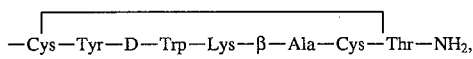
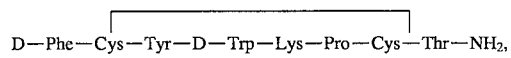
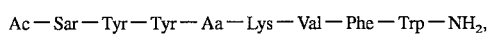
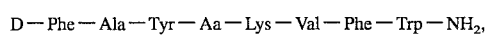
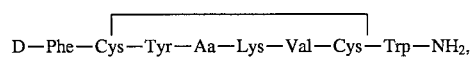
D-2-naphthyl-alanyl-
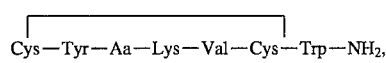
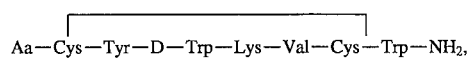
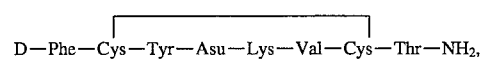
D—Phe—
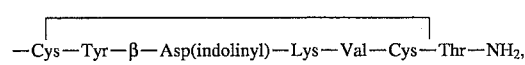

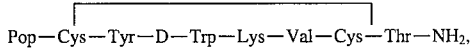
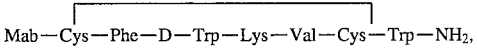
D-2-naphthyl-alanyl-
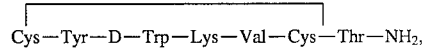
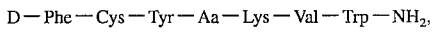
D-2-naphthyl-alanyl-
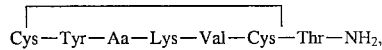
and
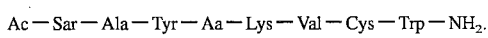

2. A pharmaceutical composition which comprises as active ingredient a heptapeptide or octapeptide amide derivative as defined in claim 1 or a pharmaceutically acceptable acid addition salt thereof in admixture with carriers and/or additives commonly used in the pharmaceutical industry.

3. A method for treating mammals, including man, suffering from tumors or from the excessive secretion of insulin, glucagon or growth hormone, consisting of administering a therapeutically effective amount of a heptapeptide or octapeptide amide derivative as defined in claim 1, or a pharmaceutically acceptable acid addition salt thereof.

4. The method of claim 3, wherein the heptapeptide amide derivative is

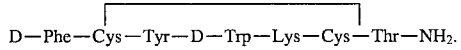

5. The method of claim 3, wherein the octapeptide amide derivative is

β-aspartyl-(indolinyl)-
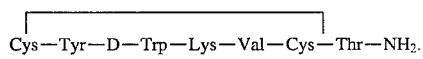

6. The composition of claim 2, wherein the octapeptide amide derivative is

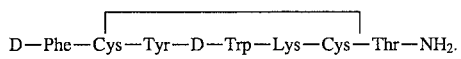

7. The composition of claim 2, wherein the octapeptide amide derivative is

β-aspartyl-(indolinyl)-

-continued

Cys—Tyr—D—Trp—Lys—Val—Cys—Thr—NH₂.

8. A heptapeptide amide derivative having the formula

D—Phe—Cys—Tyr—D—Trp—Lys—Cys—Thr—NH₂.

9. An octapeptide amide derivative having the formula

β-aspartyl-(indolinyl)-

Cys—Tyr—D—Trp—Lys—Val—Cys—Thr—NH₂.

* * * * *